United States Patent
Khan et al.

(10) Patent No.: US 10,620,119 B2
(45) Date of Patent: Apr. 14, 2020

(54) GRAPHENE FOAM BASED OPTICAL SENSOR FOR OIL EXPLORATION AND SPILLS DETECTION

(71) Applicant: King Fahd University of Petroleum and Minerals, Dhahran (SA)

(72) Inventors: Safyan A Khan, Dhahran (SA); Haider Butt, Birmingham (GB); Manzar Sohail, Dhahran (SA)

(73) Assignees: KING FAHD UNIVERSITY OF PETROLEUM AND MINERALS, Dhahran (SA); UNIVERSITY OF BIRMINGHAM, Birmingham (GB)

( * ) Notice: Subject to any disclaimer, the term of this patent is extended or adjusted under 35 U.S.C. 154(b) by 0 days.

(21) Appl. No.: 15/623,894

(22) Filed: Jun. 15, 2017

(65) Prior Publication Data

US 2018/0364161 A1 Dec. 20, 2018

(51) Int. Cl.
*G01N 21/47* (2006.01)
*C23F 1/00* (2006.01)
(Continued)

(52) U.S. Cl.
CPC ......... *G01N 21/4788* (2013.01); *C23C 16/01* (2013.01); *C23C 16/26* (2013.01);
(Continued)

(58) Field of Classification Search
CPC ........... G01N 21/4788; G01N 21/4785; G01N 33/1833; G01N 27/4145; G01N 2011/008;
(Continued)

(56) References Cited

U.S. PATENT DOCUMENTS

| 4,882,499 A | 11/1989 | Luukkala et al. |
| 5,200,615 A | 4/1993 | Hopenfeld |

(Continued)

FOREIGN PATENT DOCUMENTS

| CN | 105251459 A | 1/2016 |
| EP | 0316551 A2 | 5/1989 |

(Continued)

*Primary Examiner* — Mohamed K Amara
(74) *Attorney, Agent, or Firm* — Hauptman Ham, LLP

(57) ABSTRACT

Oil spill detection is crucial, both from an environmental perspective and the associated economic losses. Current optical oil sensing techniques, such as underwater microscopy and light scattering methods, mainly focus on detecting the properties of particles or organisms in water and often require costly equipment and sophisticated data processing. Recent studies on graphitic foam show its extraordinary pollutant absorbing properties, with high absorption weight ratios. Here we propose to produce a graphene foam based ultra-light material that changes its optical properties on absorbing oil species. The results demonstrate clear changes in optical transmission and scattering properties of graphene foam when exposed to various oils. The effective graphene foam sorbent can be easily integrated with optic fibers systems to detect the optical property variations and also to monitor oil presence/spillages remotely. Such sensors can also be used for underground oil exploration.

8 Claims, 7 Drawing Sheets
(6 of 7 Drawing Sheet(s) Filed in Color)

(51) Int. Cl.
*G01N 33/18* (2006.01)
*C23C 16/26* (2006.01)
*C23C 16/56* (2006.01)
*C23C 16/01* (2006.01)
*C23F 1/28* (2006.01)

(52) U.S. Cl.
CPC ............ *C23C 16/56* (2013.01); *C23F 1/00* (2013.01); *G01N 21/4785* (2013.01); *G01N 33/1833* (2013.01); *C23F 1/28* (2013.01)

(58) Field of Classification Search
CPC ... G01N 2291/0256; C23C 16/26; C23F 1/00; H01L 29/1606; B82Y 30/00; B82Y 15/00; B82Y 40/00; C01B 32/186; G06F 17/5009; Y10S 977/734; B01L 2300/0627; G01J 5/08; H01B 13/348; H01B 1/04; H01B 1/24; H01H 1/00
See application file for complete search history.

(56) References Cited

U.S. PATENT DOCUMENTS

| | | | |
|---|---|---|---|
| 5,264,368 A | 11/1993 | Clarke et al. | |
| 5,939,717 A | 8/1999 | Mullins | |
| 7,641,886 B2 * | 1/2010 | Tenne | B01J 19/0013 423/508 |
| 7,871,533 B1 * | 1/2011 | Haiping | B82Y 30/00 252/402 |
| 8,395,774 B2 | 3/2013 | Afzali et al. | |
| 8,709,374 B2 * | 4/2014 | Cooper | B01J 37/0215 423/447.3 |
| 9,310,285 B1 * | 4/2016 | Avouris | G01N 21/71 |
| 9,732,911 B2 * | 8/2017 | Zulfiquar | F17D 5/00 |
| 9,759,643 B2 * | 9/2017 | Avouris | G01N 21/71 |
| 9,902,918 B2 * | 2/2018 | Malshe | C10M 171/06 |
| 10,037,855 B2 * | 7/2018 | Ruoff | C01B 32/198 |
| 10,131,570 B2 * | 11/2018 | Haghighi | C23F 1/02 |
| 2006/0233692 A1 * | 10/2006 | Scaringe | B82Y 30/00 423/335 |
| 2007/0158609 A1 * | 7/2007 | Hong | B82Y 30/00 252/71 |
| 2007/0158610 A1 * | 7/2007 | Hong | C09K 5/10 252/71 |
| 2010/0204072 A1 * | 8/2010 | Kwon | C10M 125/02 508/113 |
| 2012/0032543 A1 * | 2/2012 | Chakraborty | B82Y 30/00 310/90 |
| 2014/0038862 A1 * | 2/2014 | Haque | C10M 141/10 508/128 |
| 2015/0194667 A1 | 7/2015 | Chiu et al. | |
| 2015/0284253 A1 * | 10/2015 | Zhamu | C09K 5/14 423/448 |
| 2015/0346199 A1 * | 12/2015 | Li | B01L 3/5023 506/9 |
| 2016/0004298 A1 * | 1/2016 | Mazed | G06F 3/011 345/633 |
| 2016/0121299 A1 | 5/2016 | Chang et al. | |
| 2016/0238547 A1 | 8/2016 | Park et al. | |
| 2017/0182474 A1 * | 6/2017 | Zhamu | C02F 1/681 |
| 2017/0216923 A1 * | 8/2017 | Babenko | B01J 35/0006 |
| 2018/0019070 A1 * | 1/2018 | Chai | C01B 32/23 |
| 2018/0100232 A1 * | 4/2018 | Farquhar | C23C 16/545 |
| 2018/0100233 A1 * | 4/2018 | Farquhar | B01D 1/00 |
| 2018/0230590 A1 * | 8/2018 | Farquhar | C23C 16/01 |
| 2019/0272963 A1 * | 9/2019 | Chai | C01G 39/06 |

FOREIGN PATENT DOCUMENTS

| | | |
|---|---|---|
| EP | 2439502 A1 | 4/2012 |
| JP | 01203944 A | 8/1989 |
| KR | 20160031760 A | 3/2016 |
| WO | 9721098 A1 | 6/1997 |

\* cited by examiner

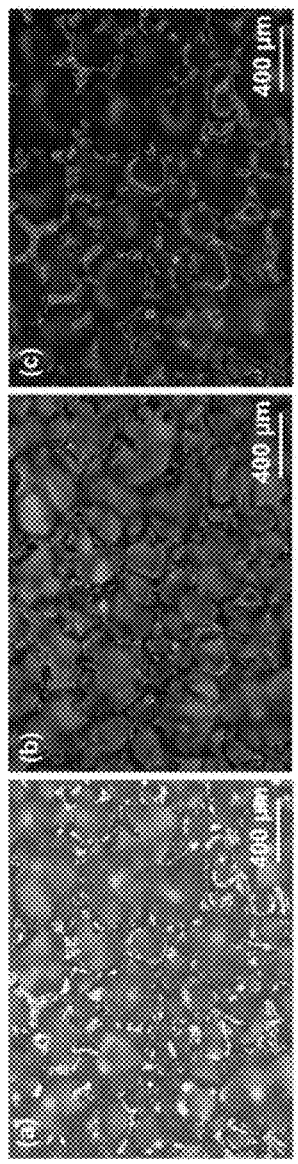
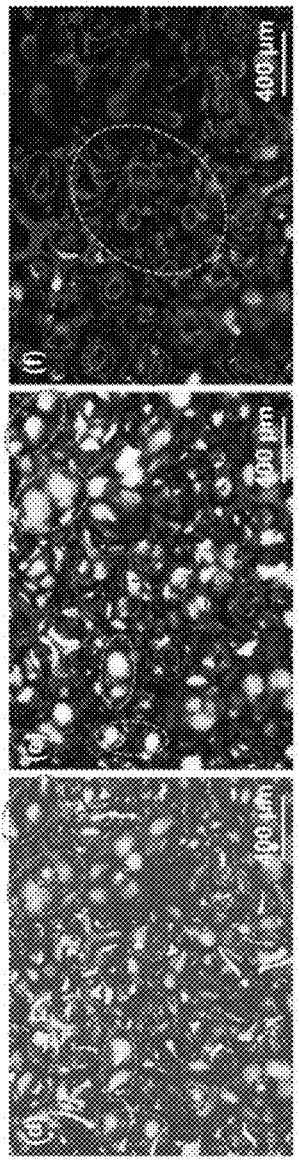
FIG. 3A R(BF)+T(BF) No Oil
FIG. 3B R(DF)+T(BF) No Oil
FIG. 3C R(DF)+T(Ph3) No Oil
FIG. 3D R(BF)+T(BF) GF+stroke oil
FIG. 3E R(DF)+T(BF) GF+stroke oil
FIG. 3F R(DF)+T(Ph3) GF+stroke oil FIG. 4A
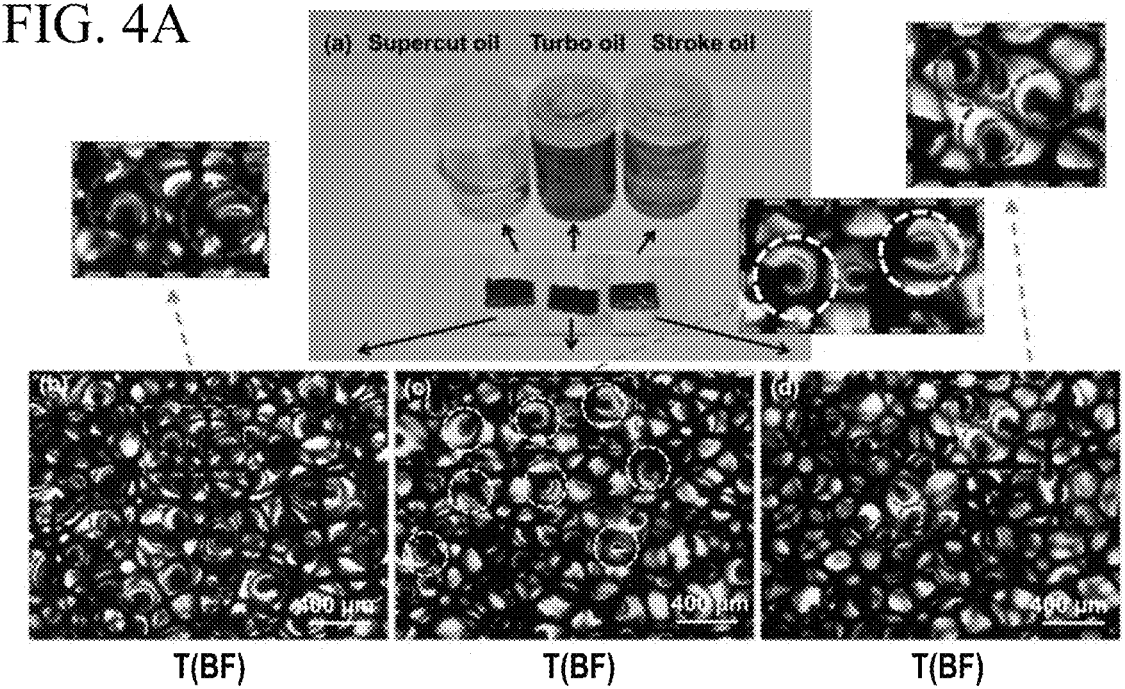
FIG. 4B  FIG. 4C  FIG. 4D
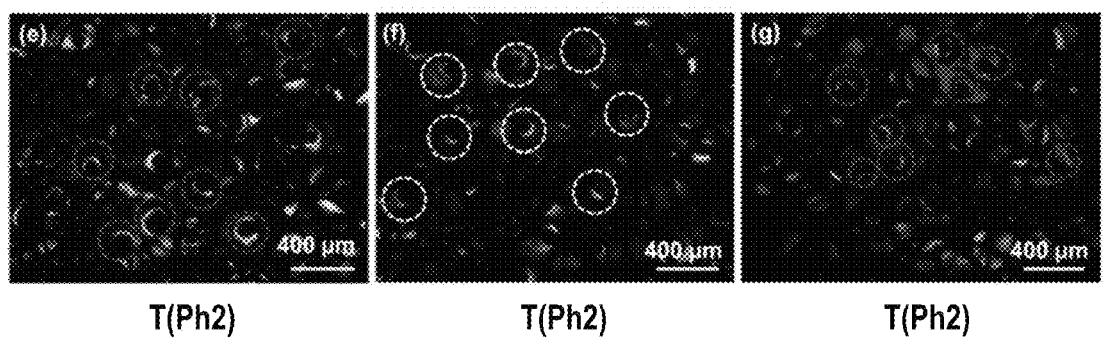
FIG. 4E  FIG. 4F  FIG. 4G GF+Wattern
T(BF)

GF+Wattern
R(DF)

GF+Wattern
T(BF)+R(DF)

GF+Spindletop
T(BF)

GF+Spindletop
R(DF)

GF+Spindletop
T(BF)+R(DF)

GF+West Texas
T(BF)

GF+West Texas
R(DF)

GF+West Texas
T(BF)+R(DF)

GF+Guffy
T(BF)

GF+Guffy
R(DF)

GF+Guffy
T(BF)+R(DF)

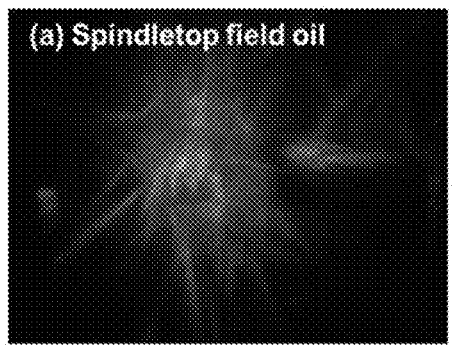
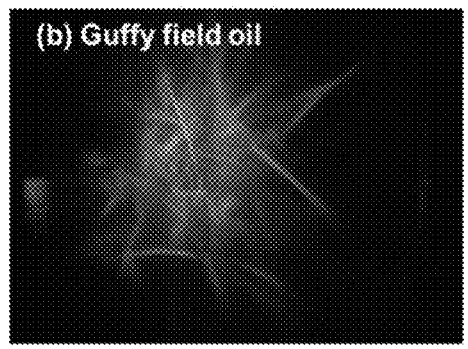
FIG. 7A    FIG. 7B
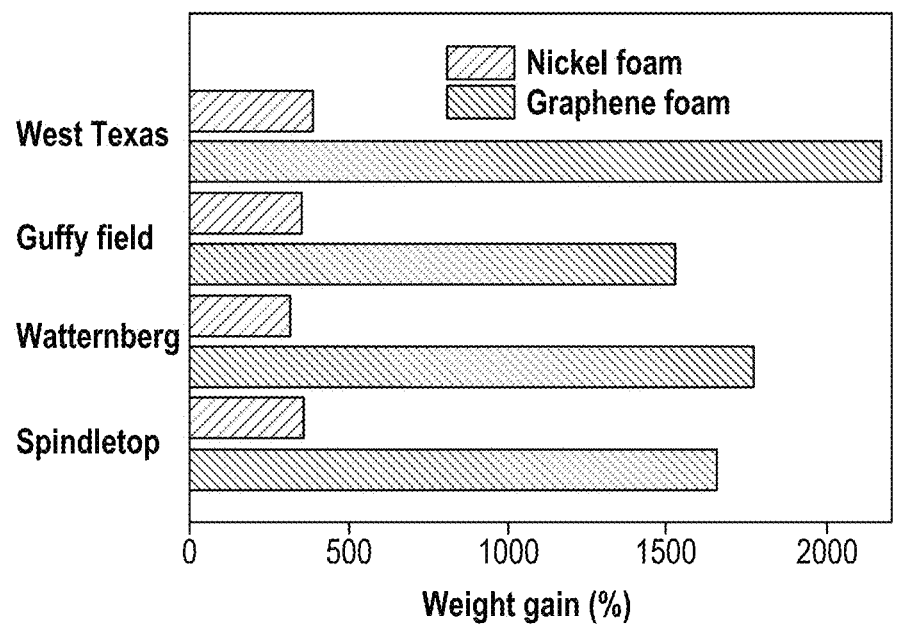
FIG. 7C

GRAPHENE FOAM BASED OPTICAL SENSOR FOR OIL EXPLORATION AND SPILLS DETECTION

FIELD OF THE INVENTION

This invention relates to a graphene foam based optical sensor for oil exploration and spills detection and more particularly to the combination of a graphene foam detector and an underwater microscope to enhance detection sensitivity.

BACKGROUND OF THE INVENTION

The leakage of oil frequently leads to disastrous consequences, resulting in massive economical losses and, more importantly environmental pollution. Developing oil sensors to diagnose an oil leak at an early stage before they cause widespread damage is crucial.[1] Petroleum hydrocarbons (HC) present a multiphase mix consisting of liquid, dissolved gaseous or solid phase in seawater [2] and direct oil sensors are used to detect methane, polyaromatic hydrocarbons, or hydrocarbons (HC) in seawater directly, while indirect oil sensors rely on discriminating the properties of the local seawater environment with and without the presence of oil.

The indirect methods may include measurement of seawater, physical properties (such as concentration of oxygen or $CO_2$), optical light scattering, and under water microscopy. An optical light scattering method [3, 4] is also used to detect the scattered light or diffraction patterns of the suspended and undissolved materials in a water sample, while underwater microscopy [5-7] is used for analyzing microscopic organisms to support dispersant injections which reduce the oil to small droplets and increase microbial degeneration.[11, 12] The existing optical methods, which focus on detecting the particles or organisms in the water generally require highly sensitive/expensive sensors to identify the small sized particles and also suffer from time consuming and complicated data processing.

As defined in Wikipedia, graphene is an allotrope of carbon in the form of a two-dimensional, atom scale, hexagonal lattice in which one atom forms each vertex. It is the basic structural element of other allotropes, including graphite, charcoal and carbon nanofibers and fullerenes. Graphene foam, taking advantages of its ultra-light weight,[13] high surface area and porous structure, has been recently proposed as a versatile and recyclable sorbent material. It shows highly efficient absorption of petroleum products (up to 86 times of its own weight), requiring no further pretreatment, which is tens of times higher than that of conventional absorbers.[14-17] Additionally, via simple heat treatment, the graphene foam can be reused up to 10 or more times without a drop in performance.[14, 15] Hence, the graphene foam can have widespread potential applications in environmental protection.

In this application, Applicants present a novel study on the optical transmission and scattering properties of graphene foam. Clear changes in these optical effects occur due to the absorption of various oil species. The presence of oil droplets in graphene foam leads to much stronger scattering effects, a change that can be easily detected remotely via optic fibers and imaging systems. Imaging of oil soaked graphene foam in multiple optical microscope detection modes demonstrates the presence of oil droplets (causing scattering) and also aid in their identification. Therefore, with the graphene foam, the efficiency of current underwater microscope and scattering based oil spill detection methods can be enhanced.

A patentability search on the invention disclosed several patents of interest. To be more specific, Geun (KR20160031760 A) discloses a gas sensor using a graphene foam to detect leakage of liquid natural gas (LNG) and liquid petroleum gas (LPG) gas. In this disclosure the graphene foam is formed by growing graphene by making the graphene absorbed to a porous nickel foam and then removing the nickel foam by etching.

Luukkala et al. (U.S. Pat. No. 4,882,499) discloses a liquid detector utilizing fiber optics, by which the presence of oils and various solvents can be detected. The detector is internally safe because the optical fiber is an insulator and may therefore be used to monitor liquids involving fire or explosive hazards. The detector may be used to detect leakage when storing oils and solvents, because it reacts most rapidly with these liquids. The detector makes use of capillarity of a sensing pick-up thereof, the optical reflection coefficient of the pick-up material changing as the pick-up material comes into contact with the liquid to be detected.

Afzali et al. (U.S. Pat. No. 8,395,774) discloses a method of using an optical sensor, the optical sensor comprising a sensing surface of graphene foam, the sensing surface located on a substrate, includes determining a first optical absorption spectrum for the graphene layer by a spectrophotometer; adding an analyte, the analyte selected to cause a shift in the first optical absorption spectrum, to the graphene layer; determining a second optical absorption spectrum for the modified graphene layer by a spectrophotometer; determining a shift between the first optical absorption spectrum and the second optical absorption spectrum; and determining a makeup of the analyte based on the determined shift.

Shioda (JP 01203944 A) discloses an oil detection sensor. An oil absorbing layer absorbs on oil, and measurement light emitted from an incidence fiber is passed through a lens in the connector on the side of an incidence surface and reflected totally by a reflecting surface, converged by the lens of the connector on the side of a projection surface, and guided to a projection fiber, so that it is confirmed that the detection surface is not covered with oil. If oil leaks by being mixed with water owing to an unexpected accident, etc., the oil absorbing layer absorbs the oil selectively without absorbing the water, so the detection surface contacts the absorbed oil. Then the detection surface of the sensor 1 enters a partial reflecting state because the oil which contacts and covers the sensor is larger in refractive index than air contacting it normally. Consequently, reflected light which is guided to the projection fiber decreases in intensity level and a photodetection part detects the oil leakage.

In conclusion, Applicants propose a simple and innovative way to detect oil environment by using graphene foam through optical imaging, as well as light scattering method. Compared with the existing methods, which detect oil emulsions or organism in the water and often involve complicated data processing, the graphene foam's performance as an oil collector can enhance the oil signal, making the detection easier, faster and economizer. Moreover, different oils in graphene foam give different colors in optical images, providing the possibility to identify the oil species. Interestingly, under microscope imaging, oil droplets can be observed in the graphene foam, which enhance the scattering effects, leading to the changes in spectral transmission. Despite the changes, the characteristic shapes of the transmission spectra remain the same, as well as the relative relationships between different oils. Finally diffraction of the oil in graphene foam was studied and results suggest that effect can be used to detect oil in conjunction with present optic fiber based oil sensors.

SUMMARY OF THE INVENTION

In essence, the present invention comprises and/or consists of a graphene foam based optical sensor and/or method for detecting and absorbing minute amounts of oil in seawater. In a first embodiment of the invention, a graphene foam based sensor comprises and/or consists of a mass of graphene foam having a pore size of about 450 µm and means for directing a sample of clean seawater onto and into said graphene foam up to its saturation condition.

In the preferred embodiment of the invention, a cleaned sample of minute amounts of oil in seawater have been cleaned by heat treatment at a temperature of between 300° C. and 400° C. for a period of 30 to 40 minutes.

Wherein said graphene foam was fabricated by chemical vapor deposition using a nickel template and removal of nickel by etching with a $FeCl_3$ solution.

Subjecting said sample of clean seawater in said graphene foam to light and magnification as viewed through an underwater microscope and reproducing a diffraction pattern from incident transmitted light on such clean seawater in graphene foam;

Means for directing an additional sample of seawater suspected of having a minute amount of leaked oil in seawater in and on said cleaned graphene foam; and, Comparing a diffraction pattern with the diffraction patterns formed by previous samples with various species of oils.

The invention will now be described in connection with the accompanying drawings wherein like reference numbers are used to identify like parts.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates optical images of graphene foam FIGS. 3A-3C without and FIGS. 3D-3F with stroke oil. Images in each column are under the same detection mode, with FIG. 3A, FIG. 3D under bright field (BF) reflected (R) and transmitted (T) light; FIG. 3B, FIG. 3E under dark field (DF) reflected and bright field transmitted light; FIG. 3C, FIG. 3F under dark field reflected light and phase contrast (Ph3) transmitted light. In FIGS. 3D-3F, oil appears as bright regions due to focusing effects. In DF mode the boundaries of the oil droplets are clearly observed (marked by red circles). All of the images were taken on the same position. Images under other modes can be found in S2-5;

FIG. 4A illustrates samples of different oils. Optical images of Graphene foam with FIG. 4B and FIG. 4E supercut oil, FIG. 4C and FIG. 4F turbo oil, FIG. 4D and FIG. 4G stroke oil. FIGS. 4B-4D are under bright field of transmitted light, while FIGS. 4E-4G are under phase contrast mode (Ph 2);

FIG. 7 illustrates diffraction patterns in response to incident red laser propagating through graphene foam soaked in FIG. 7A Spindletop field and FIG. 7B Guffy field crude oils. FIG. 7C Absorption efficiencies of Graphene and Nickel foam. Graphene foam absorbs crude oils from West Texas (21.8×), Guffy field (15.3×), Wattenberg (17.8×), and Spindletop field (16.6×) with high efficiency compared with Nickel foam, with no more than 4 times weight gain.

DETAILED DESCRIPTION OF THE PREFERRED EMBODIMENTS OF THE INVENTION

1. Introduction

The leakage of oil often leads to disastrous consequences, resulting in massive economical losses and environmental pollution. Developing oil sensor to diagnose the oil leak at early stage before they cause widespread damage is crucial. [1] Petroleum hydrocarbons (HC) present a multiphase mix consisting of liquid, dissolved gaseous or solid phase in seawater.[2] Direct oil sensors detect methane, polyaromatic hydrocarbons, or hydrocarbons (HC) in seawater directly, while indirect oil sensors rely on discriminating the properties of the local seawater environment with and without the presence of oil. The indirect methods mainly include measurement of seawater physical properties (such as concentration of oxygen or $CO_2$), optical light scattering, and under water microscopy. Optical light scattering method [3, 4] is usually used to detect the scattered light or diffraction patterns of the suspended and undissolved materials in a water sample, while underwater microscopy [5-7] is used for analyzing microscopic organism to support dispersant injection,[8-10] which reduce the oil to small droplets and increase microbial degeneration.[11, 12] The existing optical methods, which focus on detecting the particles or organisms in the water generally require highly sensitive/expensive sensors to identify the small sized particles and also suffer from time consuming and complicated data processing.

Graphene foam, taking advantages of its ultra-light weight,[13] high surface area and porous structure, has been recently proposed as a versatile and recyclable sorbent material. It shows highly efficient absorption of petroleum products and fats (up to 86 times of its own weight), requiring no further pretreatment, which is tens of times higher than that of conventional absorbers.[14-17] Additionally, via simple heat treatment, the graphene foam can be reused up to 10 times without a drop in performance.[14, 15] Hence, the graphene foam can have widespread potential applications in environmental protection as well as in oil exploration.

In this application Applicants present a novel study on the optical transmission and scattering properties of graphene foam. Clear changes in these optical effects that occur due to the absorption of various oil species were observed. The presence of oil droplets in graphene foam leads to much stronger scattering effects, a change that can be easily detected remotely via optic fibers and imaging systems. Imaging of oil soaked graphene foam in multiple optical microscope detection modes demonstrates the presence of oil droplets (causing scattering) and also aid in their identification. Therefore, with the graphene foam, the efficiency of current underwater microscope and scattering based oil spill detection methods can be enhanced.

2. Fabrication of Graphene Foam

Figure 1A:
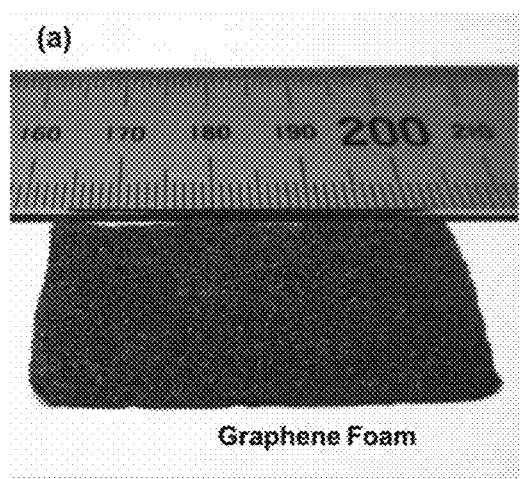
FIG. 1A illustrates optical images of graphene foam and FIG. 1B illustrates a SEM image of graphene foam.
Figure 1B:
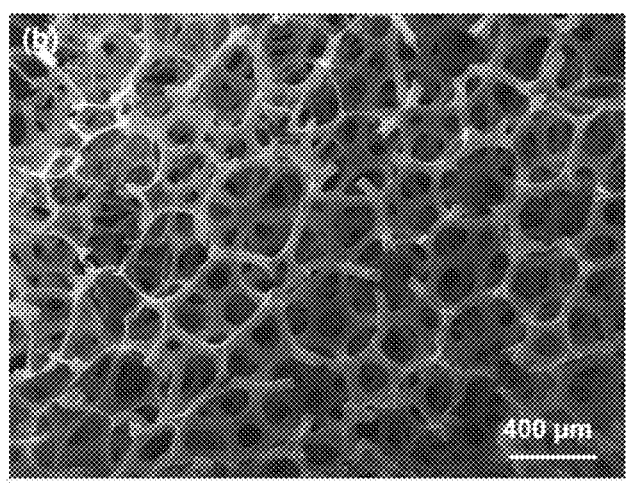

The graphene foam samples were fabricated by chemical vapor deposition (CVD) method via a nickel foam template, with a pore size of about 450 μm, area density of about 420 g/m$^2$ and a total thickness of 1.6 mm.[18] After the CVD process, the few layer graphene (FLG) covered Ni scaffold was trimmed along the edges to create access for $FeCl_3$ solution, which etched the nickel to produce the freestanding FLG foam. Then the sample was washed in deionized (DI) water and etched in 10% HCl to remove Fe. Finally, after being washed again in DI water and rinsed in iso-propanol (IPA), the graphene foam was dried in ambient air. FIGS. 1A and 1B show the optical and SEM images of graphene foam, where the multi-layer network structure can be observed.

3. Transmission Studies on Graphene Foam/Oils Composite Samples.

Figure 2B:
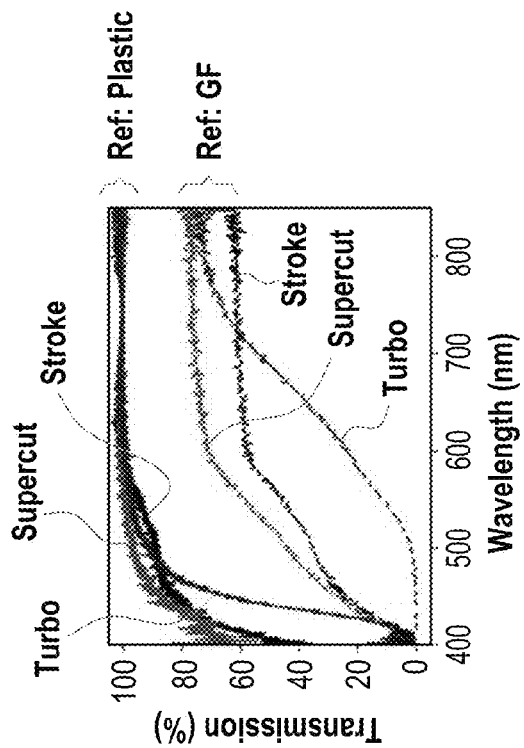
FIG. 2B illustrates transmissions of stroke oil, supercut oil, and turbo oil (solid lines) with respect to standard plastic container. Dashed lines refer to the oils soaked in graphene foam, with empty graphene foam as reference.
Figure 2D:
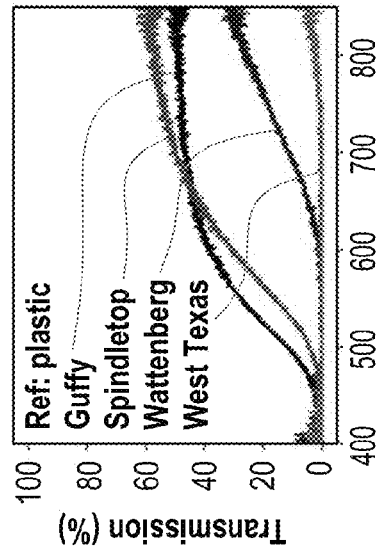
FIG. 2D illustrates transmission spectra for crude oils when soaked in graphene foam. The depth of oils in plastic container was about 2 mm.
Figure 2A:
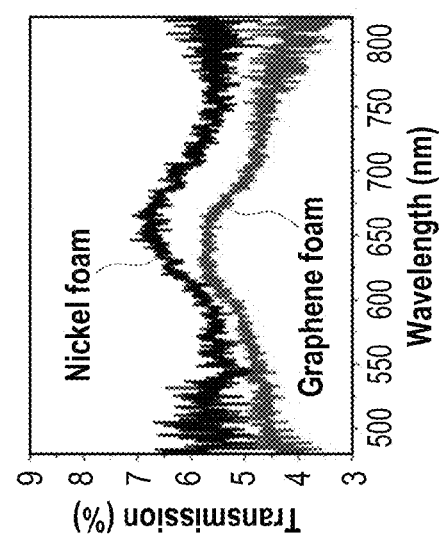
FIG. 2A illustrates transmissions of graphene and Nickel foam, with reference to glass slide. The thickness for both of the foams was near 1.6 mm.

The transmission spectra for graphene foam and three oils are shown in FIG. 2A. It can be seen that compared with glass (reference), the transmission of nickel and graphene foam are very low (less than 8%). Because of the similar structure, the transmission curves of the two foams are similar in shapes. The transmittances for various oil species (used in our study: stroke, supercut and turbo oils) were also measured, FIG. 2B. The solid lines are transmission spectra for oils in plastic container with oil depths of about 2 mm. Empty containers were used as a reference. As for the dash lines, these are transmission spectra for oils in graphene foam with reference to empty foams. The measurements were done under oil saturate conditions and it was found that the transmission through the foams was sensitive even for 0.5 μL oil, before saturation points. By combing with optical fiber sensing, it will be possible to detect minute amounts of oil and construct a graphene foam based oil sensor.

In wavelength ranges from 400 to 500 nm, all of the oils in plastic container have very low transmissions, which relate to high absorption, especially for the turbo oil, with a near zero transmission at 400 nm. The different absorptions in short wavelength regime (<550 nm) result in the difference of visual colors of the three oils, as they have almost the same transmissions, about 100%, in longer wavelengths (>600 nm).

For wavelengths at 400-600 nm, the transmission of stroke oil in graphene foam is very similar to that in plastic container, with the same characteristic shape but different intensity. The supercut oil still has a higher transmission in graphene foam than the other two oils, just as it does in plastic. The shape of transmission for turbo oil in graphene foam is very different from that in plastic, and this may due to the scattering effects.

Thus detection of oils transmission signatures can be an efficient way for differentiating the oil species. Most oils have characteristic transmission curves, although the transmission spectrum may change in the graphene foam due to the scattering effect. However, the species can be identified by comparing with transmission in transparent container. For example, it can be employed to achieve the identical characteristic behavior, or considered by the relative relationships between different oils.

Figure 2C:
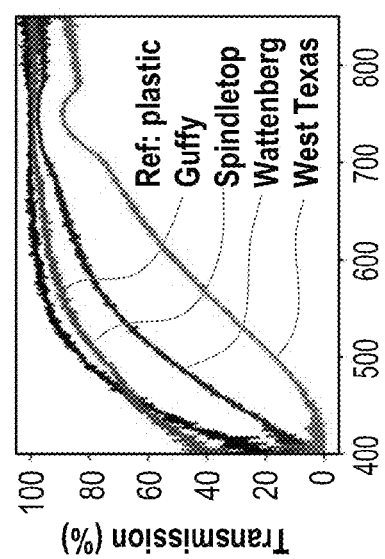
FIG. 2C illustrates transmission spectra for crude oils (including oils from Guffy, Spindletop, Wattenberg, and West Texas refineries).

Four kinds of crude oils (sourced from Wattenberg, Spindletop, West Texas, and Guffy oil fields) in graphene foam were also studied, as illustrated in FIGS. 2C-2D. In order to investigate the optical properties of crude oils in graphene foam, the transmissions measurements were performed. As shown in FIG. 2C, a low transmission efficiency in short wavelength regime (<500 nm) indicated strong corresponding absorption. Although with different colors in bottles, transmission of Spindletop oil is very close to Guffy oil, but with larger absorption in the range 470-700 nm. The transmissions of West Texas and Wattenberg oils were much lower than the other two oils in the whole visible regime.

FIG. 2D shows transmission spectra for crude oils in graphene foam, with graphene foam without oil as a reference. Negligible transmission (due to strong absorption) takes places through graphene foam containing West Texas and Wattenberg oils for light with wavelength shorter than 600 nm. Transmission for Wattenberg oil increase gradually up to 30% for larger wavelengths, while that for West Texas remains near zero. As for Spindletop oil, its transmission is higher than that of Guffy oil for red light with wavelength longer than 650 nm, but has a lower transmittance for green and yellow light. It can also be noticed that the blue light with wavelengths smaller 470 nm is absorbed by all the crude oil samples tested.

4. Graphene Foam for Oil Spill Detection Based on Optical Imaging Method.

Optical imaging measurements of graphene foam with and without oil were performed to explore the possibility of using graphene foam to detect oil environments. This study also sheds light on the optical properties and various scattering effects displayed by the graphene foam plus oils composites. A Carl Zeiss Scope A1 optical microscope was used which was equipped with several detection modes (dark and bright field). The microscope can be operated under reflected or transmitted light or with a combination of both. As for reflected (R) mode of incident light, both the bright field (BF) and dark field (DF) mode were studied, while for transmitted (T) light, bright field and phase contrast modes were studied. The phase contrast method transfers the phase-shift into intensity or color difference and has three phase modes (Ph 1-3) with varying numeral apertures adjusted by different ring diaphragms.

FIG. 3 demonstrates optical images of graphene foam with and without oil in various optical modes. Various oil species were studied analyzed but due to the most clarity the results for graphene foam soaked with stroke oil are presented in FIGS. 3D-3F under three detection modes. All the optical imaging was performed at the same position in graphene foam while illuminating with constant intensity of both reflected/transmitted light simultaneously, with identical objectives and detection modes. FIGS. 3A-3B only show the graphene foam in various optical modes. In the dark field (DF) modes the microscope blocks the normally propagating unperturbed light rays and only allows the scattered light waves through the objectives, hence the darker images. This allows the viewing of sharp edges and objects which are of the same scale as the wavelengths of light.

In FIGS. 3D-3F the presence of oil droplets can be clearly seen in the form of bright spots within graphene foam. The oil droplets lead to the local optical focusing of the transmitted light causing bright regions. The DF mode allowed the visualization of the edges of oil droplets (FIG. 3F), marked with red circles. The clear difference between a graphene/air and graphene/oil composite is the presence of these additional oil boundaries (interfaces) which lead to the scattering of incident light rays,[19] as discussed in the later experiments as well. Thus in this method, the presence of oil environments can be detected by comparing images of graphene foam with and without oils in various modes.

Moreover, the possibility of differentiating the oil species by optical images is investigated. First, graphene foam was soaked with three oils, including supercut oil, turbo oil and stroke oil, which are transparent with different colors. Then the samples were detected under transmitted light, with (b)-(d) in bright field mode and (e)-(g) phase contrast mode. Images in the same column are illustrating identical positions of the same sample. Interestingly, oil droplets were observed as small light distortions in bright field and arc-like halos in phase contrast mode. The sizes of the oil droplets are about 10 μm, thus it is expected that geometric scattering will happen when light pass through the samples.

The difference colors of the oils in the bottles indicate different absorptions characteristic. As can be seen in FIG. 4A, supercut oil is bright yellow while stroke and turbo oil are reddish. Turbo oil has strongest absorption in shorter wavelengths range thus mostly the red light passes. The colors of the oils in the graphene foam differed from their original color in the bottles; this may be due to the foam's absorption as well as the scattering effect. What can also be noticed is that the colors of supercut and stroke oils are very similar in the foam. However, more distortion can be seen when light pass though supercut oil as it is much thicker than the other two oils.

Figure 5A:
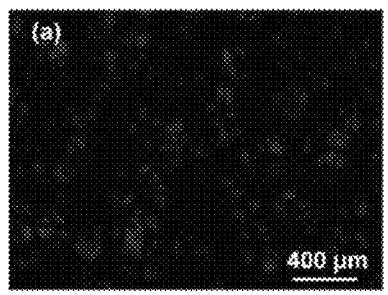
FIGS. 5A-5L illustrate optical images of graphene foam with crude oils. Each row of the images are with the same oil, with FIG. 5A Wattenberg field, FIG. 5D Spindletop field, FIG. 5G West Texas intermediate, and FIG. 5J Guffy field oil. Each column represents a different detection mode, with the first column for bright field transmitted light, second column for dark field reflected light, and the third column for both reflected (dark field) and transmitted (bright field) light.
Figure 5B:
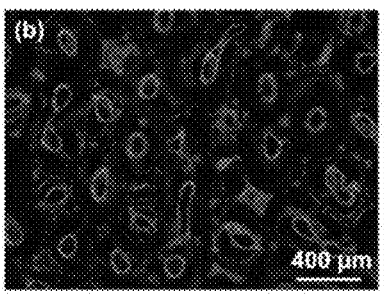
Figure 5C:
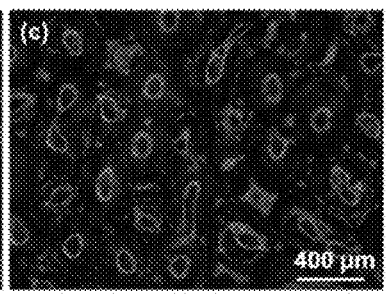
Figure 5D:
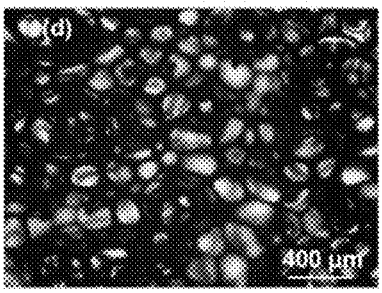
Figure 5E:
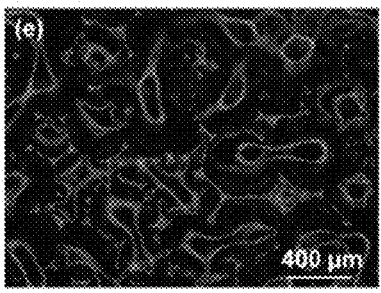
Figure 5F:
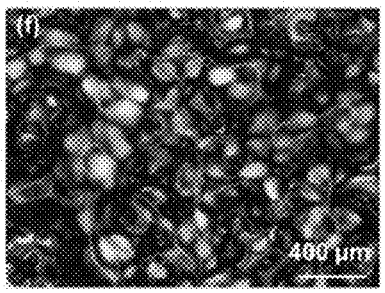
Figure 5G:
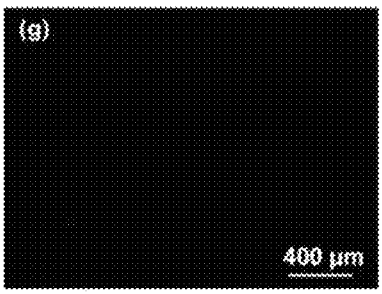
Figure 5H:
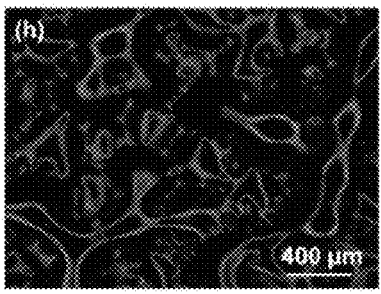
Figure 5I:
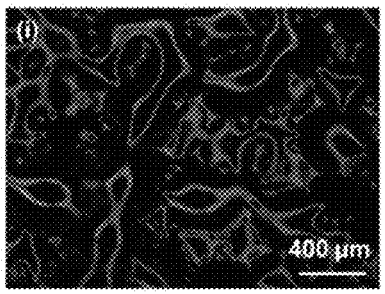
Figure 5J:
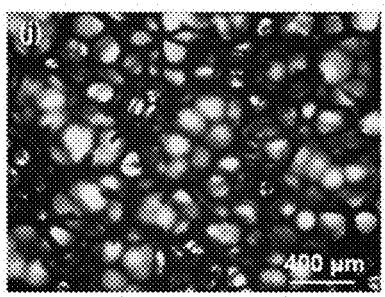
Figure 5K:
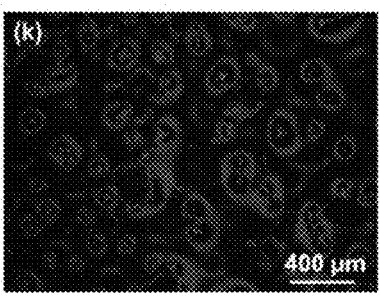
Figure 5L:
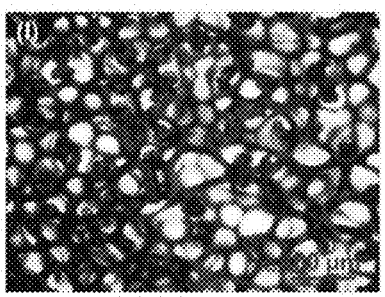

Images of crude oils in graphene foam are illustrated in FIG. 5, in which the same row are for the same oil, with FIG. 5A Wattenberg field oil, FIG. 5D Spindletop field, FIG. 5G West Texas intermediate oil, and FIG. 5J Guffy field oil. The detection modes in each column was varied, with images in the first column taken under only bright field transmitted light (T(BF)), images in the second column with dark field reflected light (R(DF)), and images in the third column with both bright field transmitted light and dark field reflected light (T(BF)+R(DF)).

In transmitted light, different oil species in graphene foam present distinct color features. The crude oils (except for Guffy field oil) were mostly black colored in the bottles and could not be differentiating by naked eyes, as demonstrated in S6. Guffy field oil in the bottle is extra light/transparent, similar to the specialized oils in FIG. 4. Thus the appearance of FIG. 5J, for Guffy field oil in graphene foam is similar to images in FIGS. 4B and 4D. As for the other three dark crude oils, the chemical and physical properties, associated with absorption and scattering effect respectively, would be different, which leads to the difference in images under transmitted light. The images for West Texas intermediate oil in FIG. 5G are totally dark, indicating a very low transmittance of visible light, while the weak red color of Wattenberg oil in image FIG. 5A suggest only a small portion of red light passes (in agreement with FIG. 2D).

The results for dark field reflected light are of interest as they present the oil distribution within the graphene foam, even when the oil is highly absorbing and dark. The distribution of Wattenberg field oil (FIG. 5B) is quite similar to Guffy field oil (FIG. 5K), with oil forming smaller droplets, compared to the larger formless shapes presented by Spindletop field and West Texas oils (FIGS. 5E and 5H). The similar reflective optical images of oils in graphene foam indicate similar surface oil distributions, which are associated with the oils physical properties, such as density, viscosity and temperature, etc. As for images in the third column, what can be seen is that they are superposition of images in the first and second columns. By combining the two optical modes, more physical and chemical properties of crude oils will be revealed. The images reveal the visible appearance of the graphene foam/crude oil composite along with the oil droplet shapes and distribution. Optical images of crude oils taken under bright field reflected light are also shown in S7.

5. Graphene Foam for Oil Spill Sensing Based on Light Diffraction.

Figure 6A:
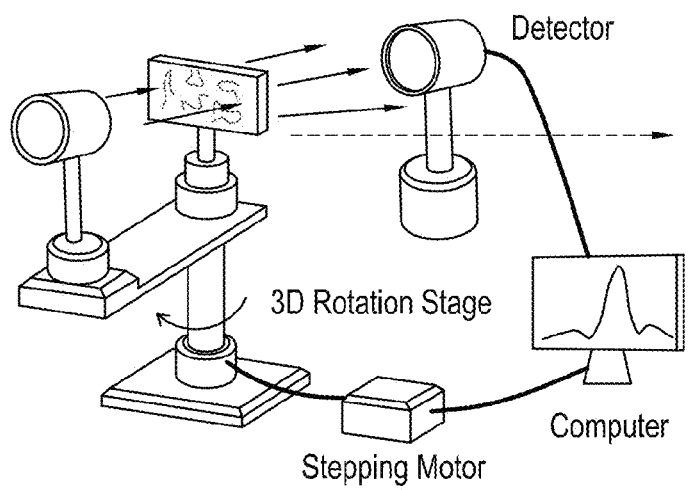
FIGS. 6A and 6B illustrate schematic and photo for the diffraction measurement set up.
Figure 6B:
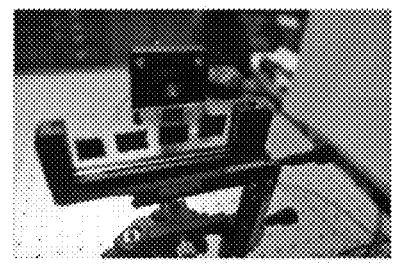

As discussed above, the oil droplets and their distribution in graphene foam may lead to light scattering. This is proven by the oil transmission spectra changes which occur when the oil species are soaked in graphene foam (FIG. 2). The imaging in various modes also suggests that oil droplets in graphene foam cause optical focusing and their boundaries lead to optical scattering effects (FIG. 4-5). To understand the effects of the presence of these droplets on the far filed transmission properties of graphene foam, optical diffractions from graphene foam (with and without oil) were studied. A customized angular diffraction set up was used with a red laser source of wavelength 650 nm. FIG. 6A depicts the schematic of the diffraction measurement set up, while FIG. 6B shows a laser beam being transmitted through a graphene foam sample. In the measurement setup, diffraction patterns were obtained by replacing the detector with a white screen and the patterns of the screen were captured by a camera. Then the screen was replaced by a detector to measure the angular optical intensity. A stepper motor was used to rotate the sample stage horizontally between −90 to 90 degrees, with 1 degree resolution.

Figure 6C:
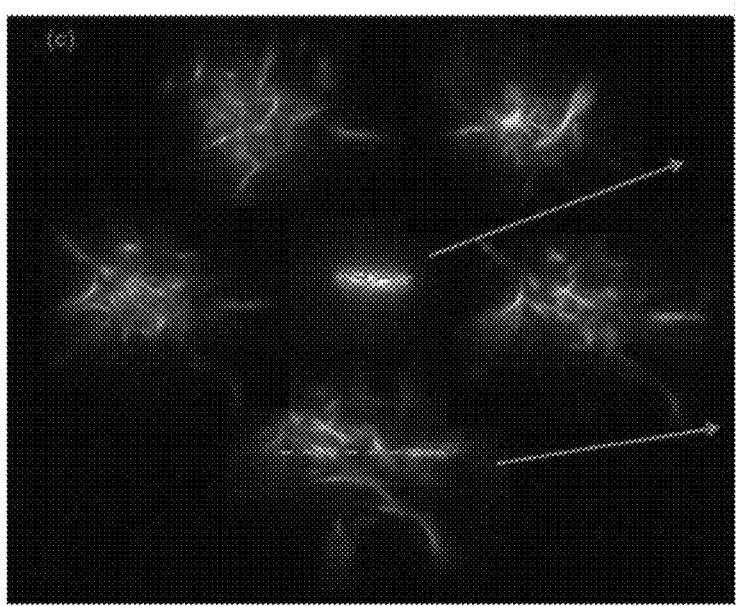
FIG. 6C Diffraction patterns when light transmitted through graphene foam without oil (middle) and with stroke oil (sides). Different patterns can be obtained at various positions of the foam. Normalized light intensity along the green line across the pattern in the middle FIG. 6D and below FIG. 6E.
Figure 6D:
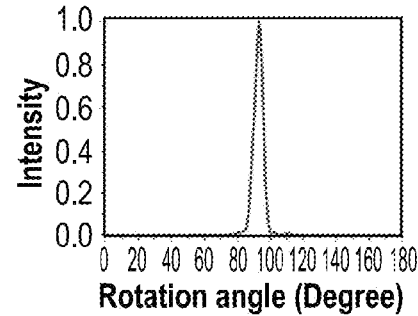
Figure 6E:
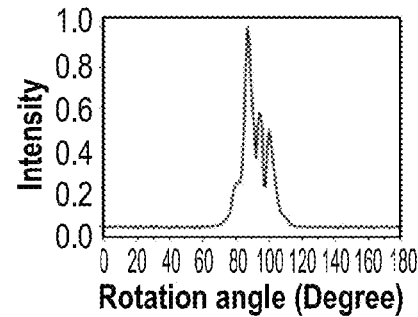

FIG. 6C demonstrates diffractions of graphene foam with and without stroke oil. In the center of FIG. 6C, the pattern represents the light passing through graphene foam without any oil, and the shape is very similar to the pattern when light passing through glass slide, without any diffraction/scattering effects. However, when the light passes through graphene foam with stroke oil (phenomenon for stroke, turbo and supercut oils are similar) the diffraction pattern changes dramatically. The patterns generated from five different regions of the sample are shown in the corners of FIG. 6C. FIGS. 6D and 6E are illustrating the normalized light intensity along the green lines across the diffraction patterns in the middle and at the bottom, respectively. For graphene foam without oil, light intensity distribution has a sharp peak in the center of the angular diffraction intensity pattern. The average pore size for graphene foam is in hundreds of microns (much larger than the wavelength of light), hence negligible diffraction/scattering of light occurs and a pronounce zero order peak (undiffracted light) is observed in the center.

However, the light intensity gets distributed in the larger degree ranges when oil is added, as shown FIG. 6E. The three peaks in this figure are consistent with the three bright spots in the bottom pattern of FIG. 6C. Optical scattering is a prominent effect that is displayed by the oil rich graphene foams. The focusing effects from each droplet and the scattering from the additional boundaries cause the spreading of the transmitted laser beams. This effect can be conveniently used for remote oil detection via optic fibers, where the presence of oil (after absorption in graphene foam) will lead to sufficient drop in transmission efficiency. The scattered rays are less to be coupled and transported by the optic fibers to the detectors; hence a transmission drop will occur and likewise the spectral signature can be used for oil species recognition.

The diffractions of crude oils in graphene foam were also studied (FIG. 7), Spindletop and Guffy oils shows distinguish diffraction effects. Because of the low transmission of Wattenberg and West Texas oil in graphene foam, no diffraction was observed. This can be explained by FIG. 2D, in which no light passes through the West Texas oil in graphene foam while no more 10% light passes through the Wattenberg oil in the foam.

To signify the superiority of graphene foam over a Ni based foam a comparison of absorption efficiencies (with crude oil samples) was performed (FIG. 7C). For each of the oil sample, graphene foam has displayed higher efficiency than Nickel foam, which has weight gains of no more than 4 times for the oils. Due to the larger density, absorption efficiencies of both foams for West Texas oil are the highest, with near 21.8 times for graphene foam and 3.8 times for Nickel foam.

CONCLUSION

In conclusion, we proposed a simple and innovative way to detect oil environment by using graphene foam through optical imaging, as well as light scattering method. Compared with the existing methods, which detect oil emulsions or organism in the water and often involve complicated data processing, the graphene foam's performance as an oil collector can enhance the oil signal, making the detection easier, faster and economizer. Moreover, different oils in graphene foam give different colors in optical images, providing the possibility to identify the oil species. Interestingly, under microscope imaging, oil droplets can be observed in the graphene foam, which enhance the scattering effects, leading to the changes in spectral transmission. Despite the changes, the characteristic shapes of the transmission spectra remain the same, as well as the relative relationships between different oils. Finally diffraction of the oil in graphene foam was studied and results suggest that effect can be used to detect oil in conjunction with present optic fiber based oil sensors.

While the invention has been defined in accordance with its preferred embodiments, it should be recognized that changes and modifications may be made therein without departing from the scope of the appended claims.

What is claimed is:

1. A graphene foam based optical method for detecting and absorbing minute amounts of oil in seawater, said method consisting of the following steps:
providing a mass of graphene foam and directing a sample of clean seawater onto and into said graphene foam up to its saturation condition,
wherein said graphene foam was fabricated by chemical vapor deposition using a nickel template and subsequent removal of nickel by etching with a FeCl3 solution so that the mass of graphene foam has a pore size of about 450 μm;
subjecting the sample of clean seawater in said graphene foam to light and magnification as viewed through an underwater microscope to obtain a first diffraction pattern or a first optical transmission and reflection image from incident light on said clean seawater sample in said graphene foam;
directing a second sample of seawater suspected of having a minute amount of a leaked oil therein onto and into said graphene foam and up to its saturation point;
subjecting the second sample of seawater to light and magnification as viewed through an underwater microscope to obtain a second diffraction pattern or a second optical transmission and reflection image from incident light on the second sample of seawater;
comparing the first diffraction pattern and the second diffraction pattern to determine if there is a presence of the leaked oil;
comparing the first optical transmission and reflection image with the second transmission and reflection image to determine if there is a presence of the minute amount of leaked oil, and,
comparing the second diffraction pattern or the second optical transmission and reflection image respectively with diffraction patterns or optical transmission and reflection images of samples of specific species of oil in a graphene foam to identify a species of the leaked oil.

2. The graphene foam based optical method for detecting and absorbing minute amounts of oil in seawater according to claim 1, in which said graphene foam has an area density of about 420 g/m2 and a thickness of about 1.6 mm.

3. The graphene foam based optical method for detecting and absorbing minute amounts of oil in seawater according to claim 1, in which the underwater microscope is operable under reflected light in bright field or dark field mode, under transmitted light in bright field mode, or under a combination thereof.

4. The graphene foam based optical method for detecting and absorbing minute amounts of oil in seawater according to claim 1, in which comparing a diffraction pattern formed of an oil containing sample is indicative of an oil species.

5. A graphene foam based optical method for detecting and absorbing minute amounts of oil in seawater, said method consisting of the following steps:
providing a mass of graphene foam and directing a sample of clean seawater onto and into said graphene foam up to its saturation condition,
wherein said graphene foam was fabricated by chemical vapor deposition using a nickel template and subsequent removal of nickel by etching with a FeCl3 solution;
subjecting the sample of clean seawater in said graphene foam to light and magnification as viewed through an underwater microscope to obtain a first diffraction pattern or a first optical transmission and reflection image from incident light on said clean seawater sample in said graphene foam;
directing a second sample of seawater suspected of having a minute amount of a leaked oil therein onto and into said graphene foam and up to its saturation point;
subjecting the second sample of seawater to light and magnification as viewed through an underwater microscope to obtain a second diffraction pattern or a second optical transmission and reflection image from incident light on the second sample of seawater;
comparing the first diffraction pattern and the second diffraction pattern to determine if there is a presence of the leaked oil;
comparing the first optical transmission and reflection image with the second transmission and reflection image to determine if there is a presence of the minute amount of leaked oil, and, comparing the second diffraction pattern or the second optical transmission and reflection image respectively with diffraction patterns or optical transmission and reflection images of samples of specific species of oil in a graphene foam to identify a species of the leaked oil.

6. The graphene foam based optical method for detecting and absorbing minute amounts of oil in seawater according to claim 5, in which said graphene foam has a pore size of about 450 μm, an area density of about 420 g/m2, and a thickness of about 1.6 mm.

7. The graphene foam based optical method for detecting and absorbing minute amounts of oil in seawater according to claim 5, in which the underwater microscope is operable under reflected light in bright field or dark field mode, under transmitted light in bright field mode, or under a combination thereof.

8. The graphene foam based optical method for detecting and absorbing minute amounts of oil in seawater according to claim 5, in which comparing a diffraction pattern formed of an oil containing sample is indicative of an oil species.

* * * * *